(12) United States Patent
Blurton et al.

(10) Patent No.: US 7,329,659 B2
(45) Date of Patent: Feb. 12, 2008

(54) SUBSTITUTED-1-PHTHALAZINAMINES AS VR-1 ANTAGONISTS

(75) Inventors: Peter Blurton, Hitchin (GB); Frank Burkamp, Bishops Stortford (GB); Stephen Robert Fletcher, Bishops Stortford (GB); A. Brian Jones, Saffron Walden (GB); Edward Giles McIver, Sawbridgeworth (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 212 days.

(21) Appl. No.: 10/555,235

(22) PCT Filed: Apr. 5, 2004

(86) PCT No.: PCT/GB2004/001942

§ 371 (c)(1),
(2), (4) Date: Oct. 31, 2005

(87) PCT Pub. No.: WO2004/099177

PCT Pub. Date: Nov. 18, 2004

(65) Prior Publication Data

US 2006/0229307 A1    Oct. 12, 2006

(30) Foreign Application Priority Data

May 9, 2003  (GB)  .................. 0310726.5

(51) Int. Cl.
| | | |
|---|---|---|
| *A61K 31/5025* | (2006.01) | |
| *A61K 31/4985* | (2006.01) | |
| *A61K 31/5355* | (2006.01) | |
| *A61K 31/519* | (2006.01) | |
| *C07D 413/04* | (2006.01) | |
| *C07D 487/04* | (2006.01) | |
| *C07D 273/30* | (2006.01) | |
| *C07D 273/32* | (2006.01) | |
| *C07D 273/34* | (2006.01) | |
| *A61P 25/04* | (2006.01) | |

(52) U.S. Cl. ............ 514/248; 514/234.5; 514/234.8; 544/117; 544/236; 544/237; 544/229

(58) Field of Classification Search ................ 544/236, 544/117; 514/234.5, 234.8, 248
See application file for complete search history.

(56) References Cited

FOREIGN PATENT DOCUMENTS

| FR | 2 043 504 A | 2/1971 |
|---|---|---|
| GB | 1 085 672 A | 10/1967 |
| WO | WO 98/46574 A | 10/1998 |
| WO | WO 03/062209 A | 7/2003 |
| WO | WO 03/099284 A | 12/2003 |

OTHER PUBLICATIONS

Wikipedia: pain or nociception. 2006.*
Wikipedia: inflammation, 2006.*
Van der Stelt, et al., Eur. J. Biochem., 271, 1827-1834, (2004).*
Chemical Abstracts Service, Yurugi, Shojiro, et al. "Synthesis of N-heterocyclic compounds VI Monosubstitution of 2-phenyl-5,8-dichloropyrimido '4,5-d-pyridazine" XP002292440 1972.

* cited by examiner

*Primary Examiner*—Mark L. Berch
*Assistant Examiner*—Cecilia M Jaisle
(74) *Attorney, Agent, or Firm*—Sylvia A. Ayler; William Krovatin

(57) ABSTRACT

The present invention provides a compound of formula (I): in which Ar and $R^1$ are phenyl or a heteroaromatic group, $R^2$ is generally hydrogen, $R^3$ is hydrogen or alkyl and X, Y and Z are generally CH or N as VR-1 antagonists; or a pharmaceutically acceptable salt thereof; pharmaceutical compositions comprising it; its use in therapy; use of it to manufacture medicaments to treat pain or inflammation; and methods of treating pain or inflammation

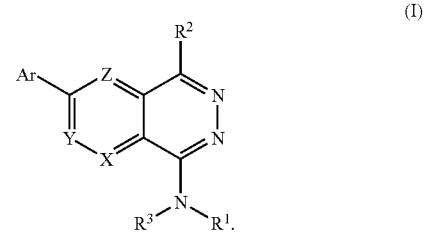

(I)

8 Claims, No Drawings

SUBSTITUTED-1-PHTHALAZINAMINES AS VR-1 ANTAGONISTS

CROSS REFERENCE TO RELATED APPLICATIONS

This application claims the benefit of Great Britain Provisional Application No. 0310726.5 filed May 9, 2003 and PCT/GB04/001942 filed May 4, 2004.

The present invention is concerned with N,6-diaryl or heteroaryl substituted-1-phthalazinamines and analogues and derivatives thereof as well as pharmaceutically acceptable salts and prodrugs thereof, which are useful as therapeutic compounds, particularly in the treatment of pain and other conditions ameliorated by the modulation of the function of the vanilloid-1 receptor (VR1).

The pharmacologically active ingredient of chilli peppers has been recognised for some time to be the phenolic amide capsaicin. The application of capsaicin to mucous membranes or when injected intradermally, causes intense burning-like pain in humans. The beneficial effects of topical administration of capsaicin as an analgesic is also well established. However, understanding of the underlying molecular pharmacology mediating these responses to capsaicin has been a more recent development.

The receptor for capsaicin, termed the vanilloid VR1 receptor, was cloned by Caterina and colleagues at UCSF in 1997 (*Nature*, 398:816, 1997). VR1 receptors are cation channels that are found on sensory nerves that innervate the skin, viscera, peripheral tissues and spinal cord. Activation of VR1 elicits action potentials in sensory fibres that ultimately generate the sensation of pain. Importantly the VR1 receptor is activated not only by capsaicin but also by acidic pH and by noxious heat stimuli. It is also sensitized by a number of inflammatory mediators and thus appears to be a polymodal integrator of painful stimuli.

The prototypical VR1 antagonist is capsazepine (Walpole et al., *J. Med. Chem.*, 37:1942, 1994)—VR1 $IC_{50}$ of 420 nM. A novel series of sub-micromolar antagonists has also been reported recently (Lee et al, *Bioorg. Med. Chem.*, 9:1713, 2001), but these reports provide no evidence for in vivo efficacy. A much higher affinity antagonist has been derived from the 'ultra-potent' agonist resiniferatoxin. Iodo-resiniferatoxin (Wahl et al., *Mol. Pharmacol.*, 59:9, 2001) is a nanomolar antagonist of VR1 but does not possess properties suitable for an oral pharmaceutical. This last is also true of the micromolar peptoid antagonists described by Garcia-Martinez (*Proc. Natl. Acad. Sci., USA*, 99:2374, 2002). Most recently International (PCT) patent publication No. WO 02/08221 has described a novel series of VR1 antagonists, which are stated to show efficacy in a number of animal models. We herein describe another novel series of VR1 modulators. These comprise predominantly VR1 antagonists but encompass VR1 partial antagonists and VR1 partial agonists. Such compounds have been shown to be efficacious in animal models of pain. Other VR1 antagonists are disclosed in WO 03/062209 (Neurogen Corporation).

The present invention provides compounds of formula (I):

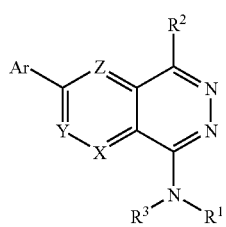

(I)

wherein Ar is phenyl, a six-membered heteroaromatic group containing one, two or three nitrogen atoms or a five-membered heteroaromatic group containing one, two, three or four heteroatoms chosen from oxygen, nitrogen and sulfur, at most one heteroatom being oxygen or sulfur, Ar being optionally substituted with one, two or three groups independently chosen from halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, amino, halo$C_{1-6}$alkyl, halo$C_{2-6}$alkenyl, halo$C_{2-6}$alkynyl, hydroxy$C_{1-6}$alkyl, hydroxy$C_{2-6}$alkenyl, hydroxy$C_{2-6}$alkynyl, cyano, nitro, amino$C_{1-6}$alkyl, amino$C_{2-6}$alkenyl, amino$C_{2-6}$alkynyl, $C_{1-6}$alkylsulfonyl, $C_{1-6}$alkylsulfinyl, $C_{1-6}$alkylthio, $C_{1-6}$alkoxycarbonyl, halo$C_{1-6}$alkoxy, halo$C_{2-6}$alkenyloxy, halo$C_{2-6}$alynyloxy, $NR^4R^5$, $CONR^4R^5$ or $CO_2NR^4R^5$ where each $R^4$ and $R^5$ is independently hydrogen or $C_{1-6}$alkyl;

$R^1$ is phenyl, a six-membered heteroaromatic group containing one, two or three nitrogen atoms or a five-membered heteroaromatic group containing one, two, three or four heteroatoms chosen from oxygen, nitrogen and sulfur, at most one heteroatom being oxygen or sulfur, Ar being optionally substituted with one, two or three groups independently chosen from halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, amino, halo$C_{1-6}$alkyl, halo$C_{2-6}$alkenyl, halo$C_{2-6}$alkynyl, hydroxy$C_{1-6}$alkyl, hydroxy$C_{2-6}$alkenyl, hydroxy$C_{2-6}$alkynyl, cyano, nitro, amino$C_{1-6}$alkyl, amino$C_{2-6}$alkenyl, amino$C_{2-6}$alkynyl, $C_{1-6}$alkylsulfonyl, $C_{1-6}$alkylsulfinyl, $C_{1-6}$alkylthio, $C_{1-6}$alkoxycarbonyl, halo$C_{1-6}$alkoxy, halo$C_{2-6}$alkenyloxy, halo$C_{2-6}$alkynyloxy, $NR^4R^5$, $CONR^4R^5$ or $CO_2NR^4R^5$ where $R^4$ and $R^5$ are as defined above;

$R^2$ is hydrogen, halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $NR^6R^7$ where $R^6$ and $R^7$ are, independently, hydrogen, $C_{1-6}$alkyl or $C_{1-6}$hydroxyalkyl, or $R^6$ and $R^7$, together with the nitrogen atom to which they are attached form a 4, 5 or 6-membered stable heterocycle optionally containing an oxygen ring atom;

$R^3$ is hydrogen or $C_{1-6}$alkyl;

each X, Y and Z is N or $CR^8$ where $R^8$ is hydrogen, halogen or $C_{1-6}$alkyl;

or a pharmaceutically acceptable salt thereof.

Ar is preferably unsubstituted or substituted by one or two groups. Ar may be substituted by one group. Ar may be unsubstituted.

Any substituents on Ar are preferably independently chosen from halogen, hydroxy, $C_{1-6}$alkyl, hydroxy$C_{1-6}$alkyl, halo$C_{1-6}$alkyl, $C_{1-6}$alkoxy, cyano and $C_{1-6}$alkoxycarbonyl. Any substituents are more preferably fluorine, $C_{1-4}$alkyl, hydroxy$C_{1-4}$alkyl, halo$C_{1-4}$alkyl $C_{1-4}$alkoxy, cyano or $C_{1-4}$alkoxycarbonyl. Examples of substituents are trifluoromethyl, fluorine, methyl, methoxy, 2-hydroxyisopropyl, cyano, ethoxycarbonyl and 2-fluoroisopropyl.

Ar is preferably phenyl or a 6-membered heteroaromatic ring. Ar is particularly phenyl, pyridyl, imidazolyl, pyrazinyl, pyridazinyl or pyrimidinyl.

Particular embodiments of Ar include 3-trifluoromethylpyrid-2-yl, 3-fluoropyrid-2-yl, 3-methylpyrid-2-yl, pyrid-2-yl, 1-methylimidazol-2-yl, 3-methoxypyrid-2-yl, 3-(2-hydroxyisopropyl)pyrid-2-yl, 5-trifluoromethylpyrid-2-yl, 6-trifluoromethylpyrid-2-yl, 4-trifluoromethylpyrid-2-yl, 4-methylpyridazin-3-yl, 5-methylpyrimidin-4-yl, 2-methylpyrazin-3-yl, 4-trifluoromethylpyridazin-3-yl, 2-methoxyphenyl, 2-cyanophenyl, 3,5-difluoropyrid-2-yl, 3-cyanopyrid-2-yl, 3-ethoxycarbonylpyrid-2-yl and 3-(2-fluoroisopropyl)pyrid-2-yl.

It is preferred that Ar is pyridyl, and preferably monosubstituted.

It is preferred that Ar be monosubstituted at the ring position adjacent to the point of attachment of Ar to the rest of the molecule.

$R^1$ is preferably unsubstituted or substituted by halogen, $C_{1-6}$alkyl, halo$C_{1-6}$alkyl, halo$C_{1-6}$alkoxy or $C_{1-6}$alkoxycarbonyl. The substituents on $R^1$ are more preferably fluorine, $C_{1-4}$alkyl, halo$C_{1-4}$alkyl, halo$C_{1-4}$alkoxy or $C_{1-4}$alkoxycarbonyl. Examples of substituents include trifluoromethyl, tertiarybutyl, trifluoromethoxy, fluorine and ethoxycarbonyl.

$R^1$ is preferably phenyl or pyridyl, particularly phenyl.

$R^1$ is preferably monosubstituted. The substituent is preferably para to the point of attachment of $R^1$ to the rest of the molecule.

Particular embodiments of $R^1$ include 4-trifluoromethylphenyl, 4-tert-butylphenyl, 4-trifluoromethoxyphenyl, 4-fluorophenyl, 4-ethoxycarbonylphenyl and 5-trifluoromethylpyrid-2-yl.

$R^2$ is preferably hydrogen, $C_{1-6}$alkoxy or $NR^6R^7$. $R^2$ is more preferably hydrogen, $C_{1-4}$alkoxy, di($C_{1-4}$alkyl)amino or morpholino. $R^2$ may be hydrogen, methoxy, dimethylamino or morpholino. $R^2$ may be hydrogen.

$R^3$ is preferably hydrogen.

$R^4$ and $R^5$ are preferably hydrogen or methyl, particularly hydrogen.

Preferably none or one of X, Y and Z is N and the others are $CR^8$. $R^8$ is preferably hydrogen. Preferably Z is N and X and Y are CH.

Preferred subclasses of compounds are shown below:

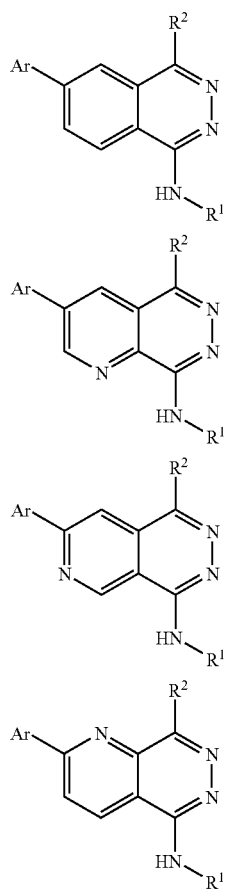

(IA)

(IB)

(IC)

(ID)

in which $R^1$, $R^2$ and Ar are as defined above, including the preferred definitions.

Thus, in the compounds of formulae IA, IB, IC and ID:

Ar is phenyl or a six-membered heteroaromatic ring optionally substituted with one or two substituents independently chosen from halogen, hydroxy, $C_{1-6}$alkyl, hydroxy$C_{1-6}$alkyl, halo$C_{1-6}$alkyl, $C_{1-6}$alkoxy, cyano and $C_{1-6}$alkylcarbonyl;

$R^1$ is phenyl or pyridyl, particularly phenyl, monosubstituted by halogen, $C_{1-6}$alkyl, halo$C_{1-6}$alkyl, halo$C_{1-6}$alkoxy or $C_{1-6}$alkoxycarbonyl; and $R^2$ is hydrogen, $C_{1-4}$alkoxy, di($C_{1-4}$alkyl)amino or morpholino.

In one embodiment the compound of formula I is a free base.

Particular embodiments of the invention include:

N-(4-trifluoromethylphenyl)-6-(3-trifluoromethyl-2-pyridinyl)-1-phthalazinamine;

6-(3-fluoro-2-pyridinyl)-N-(4-trifluoromethylphenyl)-1-phthalazinamine;

N-(4-(tert-butylphenyl)-6-(3-trifluoromethyl-2-pyridinyl)-1-phthalazinamine;

6-(3-methyl-2-pyridinyl)-N-(4-(trifluoromethylphenyl)-1-phthalazinamine;

6-(3-methyl-2-pyridinyl)-N-(4-trifluoromethoxyphenyl)-1-phthalazinamine;

6-(2-pyridinyl)-N-(4-trifluoromethylphenyl)-1-phthalazinamine;

N-(4-trifluoromethylphenyl)-2-(3-trifluoromethyl-2-pyridinyl)pyrido[2,3-d]pyridazin-5-amine;

6-(1-methyl-1H-imidazol-2-yl)-N-(4-trifluoromethylphenyl)-1-phthalazinamine;

4-methoxy-6-(3-methyl-2-pyridinyl)-N-(4-trifluoromethylphenyl)-1-phthalazinamine;

7-(3-methyl-2-pyridinyl)-N-(4-trifluoromethylphenyl)pyrido[3,4-d]pyridazin-4-amine;

4-dimethylamino-6-(3-methylpyridin-2-yl)-N-(4-trifluoromethylphenyl)-1-phthalazinamine;

6-(3-methylpyridin-2-yl)-4-(morpholin-4-yl)-N-(4-trifluoromethylphenyl)-1-phthalazinamine;

6-(3-methoxy-2-pyridinyl)-N-(4-trifluoromethylphenyl)-1-phthalazinamine;

2-{2-[1-(4-trifluoromethylphenylamino)phthalazin-6-yl]pyridin-3-yl}propan-2-ol;

N-(4-trifluoromethylphenyl)-6-(5-trifluoromethyl-2-pyridinyl)-1-phthalazinamine;

N-(4-trifluoromethylphenyl)-6-(6-trifluoromethyl-2-pyridinyl)-1-phthalazinamine;

N-(4-trifluoromethylphenyl)-6-(4-trifluoromethyl-2-pyridinyl)-1-phthalazinamine;

6-(4-methyl-3-pyridazinyl)-N-(4-trifluoromethylphenyl)-1-phthalazinamine;

6-(5-methyl-4-pyrimidinyl)-N-(4-trifluoromethylphenyl)-1-phthalazinamine;

6-(3-methyl-2-pyrazinyl)-N-(4-trifluoromethylphenyl)-1-phthalazinamine;

N-(4-trifluoromethylphenyl)-6-(4-trifluoromethyl-3-pyridazinyl)-1-phthalazinamine;

N-(4-tert-butylphenyl)-6-(3-methyl-2-pyridinyl)-1-phthalazinamine hydrochloride;

N-(4-fluorophenyl)-6-(3-methyl-2-pyridinyl)-1-phthalazinamine;

6-(2-methoxyphenyl)-N-(4-trifluoromethylphenyl)-1-phthalazinamine;

6-(2-cyanophenyl)-N-(4-trifluoromethylphenyl)-1-phthalazinamine;

3-(3-methylpyridin-2-yl)-N-(4-trifluoromethylphenyl)pyrido[2,3-d]pyridazin-8-amine;

N-(4-ethoxycarbonylphenyl)-6-(3-methyl-2-pyridinyl)-1-phthalazinamine;
6-(3,5-difluoro-2-pyridinyl)-N-(4-trifluoromethylphenyl)-1-phthalazinamine;
6-(3-cyano-2-pyridinyl)-N-(4-trifluoromethylphenyl)-1-phthalazinamine;
6-(3-ethoxycarbonyl-2-pyridinyl)-N-(4-trifluoromethylphenyl)-1-phthalazinamine;
6-(3-(1-fluoro-1-methylethyl)-2-pyridinyl)-N-(4-trifluoromethylphenyl)-1-phthalazinamine;
N-(4-trifluoromethylphenyl)-2-(3-chloro-2-pyridinyl)pyrido[2,3-d]pyridazin-5-amine; and
N-(5-trifluoromethyl-2-pyridinyl)-2-(3-trifluoromethyl-2-pyridinyl)pyrido[2,3-d]pyridazin-5-amine;
or a pharmaceutically acceptable salt thereof.

As used herein, the term "alkyl" or "alkoxy" as a group or part of a group means that the group is straight or branched. Examples of suitable alkyl groups include methyl ethyl n-propyl, i-propyl, n-butyl s-butyl and t-butyl. Examples of suitable alkoxy groups include methoxy, ethoxy, n-propoxy, i-propoxy, n-butoxy, s-butoxy and t-butoxy. "Alkylthio" shall be construed in an analogous manner.

As used herein, the term "hydroxy$C_{1-6}$alkyl" means a $C_{1-6}$alkyl group in which one or more (in particular 1 to 3, and especially 1) hydrogen atoms have been replaced by hydroxy groups. Particularly preferred are hydroxy$C_{1-3}$alkyl groups, for example, $CH_2OH$, $CH_2CH_2OH$, $CH(CH_3)OH$ or $C(CH_3)_2OH$, and most especially $CH_2OH$. "Aminoalkyl" shall be construed in an analogous manner.

As used herein, the terms "halo$C_{1-6}$alkyl" and "halo $C_{1-6}$alkoxy" means a $C_{1-6}$alkyl or $C_{1-6}$alkoxy group in which one or more (in particular, 1 to 3) hydrogen atoms have been replaced by halogen atoms, especially-fluorine or chlorine atoms. Preferred are fluoro$C_{1-6}$alkyl and fluoro$C_{1-6}$alkoxy groups, in particular, fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$ and $OCF_3$.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein, the term "halogen" means fluorine, chlorine, bromine and iodine. The most preferred halogens are fluorine and chlorine, especially fluorine.

When used herein, the term "$C_{1-6}$alkoxycarbonyl" denotes a $C_{1-6}$alkoxy or a halo$C_{1-6}$alkoxy radical attached via the oxygen atom thereof to a carbonyl (C=O) radical thus forming a $C_{1-6}$alkoxycarbonyl or halo$C_{1-6}$alkoxycarbonyl radical. Suitable examples of such esterified carboxy groups include, for example, methoxycarbonyl, ethoxycarbonyl, propoxycarbonyl, isopropoxycarbonyl and tert-butoxycarbonyl.

Examples of 6-membered heterocycles are pyridine, pyrimidine, pyrazine, pyridazine and triazine.

Examples of 5-membered heterocycles are thiophene, furan, pyrrole, imidazole, pyrazole, oxazole, isoxazole, thiazole, isothiazole, 1,2,3-triazole, 1,2,4-triazole, oxadiazole, thiadiazole and tetrazole.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts. Particularly preferred are the hydrochloride and besylate, particularly besylate, salts.

The salts may be formed by conventional means, such as by reacting the free base form of the compound of formula (a) with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention also includes within its scope N-oxides of the compounds of formula (I) above. In general, such N-oxides may be formed on any available nitrogen atom. The N-oxides may be formed by conventional means, such as reacting the compound of formula (I) with oxone in the presence of wet alumina.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention. Furthermore, the compounds of formula (I) may also exist in tautomeric forms and the invention includes within its scope both mixtures and separate individual tautomers.

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, sterile parenteral solutions or suspensions, metered aerosol or liquid sprays, drops, ampoules, auto-injector devices, suppositories, creams or gels; for oral parenteral intrathecal, intranasal, sublingual rectal or topical administration, or for administration by inhalation or insufflation. Oral compositions such as tablets, pills, capsules or wafers are particularly preferred. For preparing solid compositions such as tablets, the principal active ingredient is mixed with a pharmaceutical carrier, e.g. conventional tabletting ingredients such as corn starch, lactose, sucrose, sorbitol talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation composition is then subdivided into unit dosage forms of the type described above containing from 0.1 to about 500 mg of the active ingredient of the present invention. Favoured unit dosage forms contain from 1 to 500 mg, for example 1, 5, 10, 25, 50, 100, 300 or 500 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of painful conditions such as those listed below, a suitable dosage level is about 1.0 mg to 15 g per day, preferably about 5.0 mg to 1 g per day, more preferably about 5 mg to 500 mg per day, especially 10 mg to 100 mg per day. The compounds may be administered on a regimen of 1 to 4 times per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The invention further provides a compound of formula (I) as defined above, or a pharmaceutically acceptable salt thereof, for use in treatment of the human or animal body. Preferably, said treatment is for a condition which is susceptible to treatment by modulation (preferably antagonism) of VR1 receptors.

The compounds of the present invention will be of use in the prevention or treatment of diseases and conditions in which pain and/or inflammation predominates, including chronic and acute pain conditions. Such conditions include rheumatoid arthritis; osteoarthritis; post-surgical pain; musculo-skeletal pain, particularly after trauma; spinal pain; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, for example, odontalgia, abdominal pain, gynaecological pain, for example, dysmenorrhoea, pain associated with cystitis and labour pain, chronic pelvic pain, chronic prostatitis and endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; itching conditions including pruritus, itch due to hemodialysis, and contact dermatitis; pain (as well as broncho-constriction and inflammation) due to exposure (e.g. via ingestion, inhalation, or eye contact) of mucous membranes to capsaicin and related irritants such as tear gas, hot peppers or pepper spray; neuropathic pain conditions such as diabetic neuropathy, chemotherapy-induced neuropathy and post-herpetic neuralgia; "non-painful" neuropathies; complex regional pain syndromes; pain associated with carcinoma, often referred to as cancer pain; central nervous system pain, such as pain due to spinal cord or brain stem damage, low back pain, sciatica and ankylosing spondylitis; gout; scar pain; irritable bowel syndrome; inflammatory bowel disease; urinary incontinence including bladder detrusor hyper-reflexia and bladder hypersensitivity; respiratory diseases including chronic obstructive pulmonary disease (COPD), chronic bronchitis, cystic fibrosis, asthma and rhinitis, including allergic rhinitis such as seasonal and perennial rhinitis, and non-allergic rhinitis; autoimmune diseases; and immunodeficiency disorders.

Thus, according to a further aspect, the present invention provides a compound of formula (I) for use in the manufacture of a medicament for the treatment or prevention of physiological disorders that may be ameliorated by modulating VR1 activity.

The present invention also provides a method for the treatment or prevention of physiological disorders that may be ameliorated by modulating VR1 activity, which method comprises administration to a patient in need thereof of an effective amount of a compound of formula (I) or a composition comprising a compound of formula (I).

According to a further or alternative aspect, the present invention provides a compound of formula (I) for use in the manufacture of a medicament for the treatment or prevention of a disease or condition in which pain and/or inflammation predominates.

The present invention also provides a method for the treatment or prevention of a disease or condition in which pain and/or inflammation predominates, which method comprises administration to a patient in need thereof of an effective amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment or prevention of pain and/or inflammation, a compound of the present invention may be used in conjunction with other analgesics, such as acetaminophen (paracetamol), aspirin and other NSAIDs, including selective cyclooxygenase-2 (COX-2) inhibitors, as well as opioid analgesics, especially morphine, NR2B antagonists, bradykinin antagonists, anti-migraine agents, anticonvulsants such as oxcarbazepine and carbamazepine, antidepressants (such as TCAs, SSRIs, SNRIs, substance P antagonists, etc.), spinal blocks, gabapentin, pregabalin and asthma treatments (such as $\theta_2$-adrenergic receptor agonists or leukotriene $D_4$ antagonists (e.g. montelukast).

Specific anti-inflammatory agents include diclofenac, ibuprofen, indomethacin, nabumetone, ketoprofen, naproxen, piroxicam and sulindac, etodolac, meloxicam, rofecoxib, celecoxib, etoricoxib, parecoxib, valdecoxib and tilicoxib. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Suitable anti-migraine agents of use in conjunction with a compound of the present invention include CGRP-antagonists, ergotamines or 5-$HT_1$ agonists, especially sumatriptan, naratriptan, zolmatriptan or rizatriptan.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of a disease or condition in which pain and/or inflammation predominates.

The compounds of formula 1 can be made by reacting a compound of formula II with a compound of formula III:

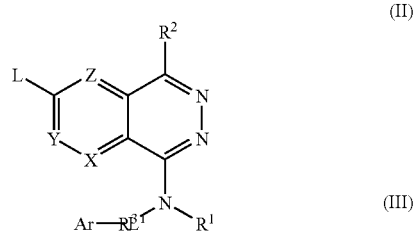

in which Ar, $R^1$, $R^2$, $R^3$, X, Y and Z are as defined above and one of L and $L^1$ is Cl or Sn(alkyl)$_3$, for example Sn(methyl)$_3$ or Sn(n-butyl)$_3$, and the other is bromine or chlorine. When L or $L^1$ is Cl it can be initially converted into a group B(OH)$_2$ under conditions suitable for a Suzuki Coupling Reaction (for review, see for instance A. Suzuki, *Pure Appl. Chem.*, 1991, 63, 419-422), for example, in the presence of a palladium catalyst such as tetrakis(triphenylphosphine) palladium(0), tris(dibenzylideneacetone)dipalladium(0), (1,1'-bis(diphenylphosphino)ferrocene)dichloropalladium or dichloro-(1,4-bis(diphenylphosphino)butane)palladium, in a suitable solvent such as an ether, for example, dimethoxyethane or dioxane or an aromatic hydrocarbon, for example toluene, at an elevated temperature and in the presence of a base such as sodium carbonate. Where L or $L^1$ is Sn(alkyl)$_3$, the reaction is conveniently effected under conditions suitable for a Stille Coupling Reaction (for review, see for instance J. K. Stille, *Angew. Chem. Int. Ed.*, 1986, 25, 508-524), for example, in the presence of a palladium catalyst such as tetrakis(triphenylphosphine)palladium(0) or bis(triphenylphosphine)palladium(II) chloride, in a suitable solvent such as an ether, for example dioxane, or an aromatic hydrocarbon, for example, toluene, at an elevated temperature, and in the presence of catalysts such as LiCl and CuI.

Compounds of formula II can be made by reacting a compound of formula IV with a compound of formula HNR$^1$R$^3$:

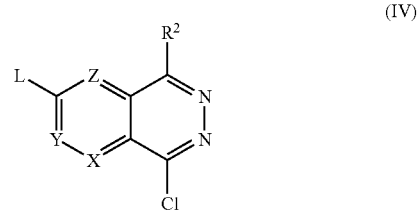

in which L is Br and X, Y, Z, $R^1$, $R^2$ and $R^3$ are as defined above. The reaction is generally carried out in a solvent such as dioxane in the presence of an acid such as hydrochloric acid for about 30 to 60 minutes at about reflux.

Compounds of formula I can also be made by reacting a compound of formula V with a compound of formula HNR$^1$R$^3$:

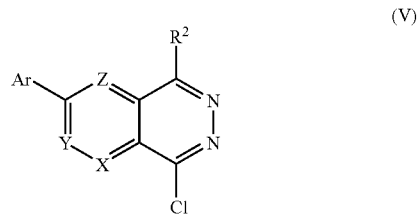

in which Ar, X, Y, Z, $R^1$, $R^2$ and $R^3$ are as defined under similar conditions to the preceding reaction.

The compound of formula V can be made by reacting the fused pyridazin-5(6H)-one precursor with phosphorus oxychloride at about reflux or 100° C. for about one to five hours.

This compound can be made by reacting a compound of formula VI:

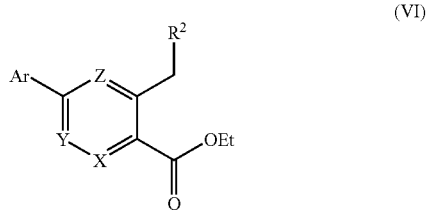

in which Ar, $R^2$, X, Y and Z are as defined above, by the free radical addition of bromine using for example, N-bromosuccinimide and AIBN or benzoyl peroxide in a non-protic solvent such as carbon tetrachloride at about reflux in the presence of light for about 10 to 48 hours, followed by treating with hydrazine hydrate in a solvent such as ethanol at about reflux for about 18 hours.

Compounds of formula VI in which $R^2$ is H, Z is N and X and Y are CH, can be made by reacting a compound of formula ArCN in which Ar is as defined above with methylmagnesium iodide generally in a solvent such as tetrahydrofuran at about room temperature for about one hour under an inert atmosphere, to produce a compound of formula $ArC(O)CH_3$. This compound is reacted successively with dimethylformamide dimethylacetal generally in a microwave at about 160° C. for about 5 minutes and then with ethyl 3-aminocrotonate in a solvent such as glacial acetic acid at about reflux for about six hours.

Compounds of formula IV in which $R^2$ is chlorine can be made by reacting a compound of formula VII:

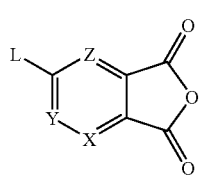

(VII)

in which L is bromine and X, Y and Z are as defined above with hydrazine hydrate generally in the presence of acetic acid at about 80° C. for several hours followed by reaction with one equivalent of phosphorus oxychloride generally in the presence of a base such as diisopropylamine for about three hours at about reflux.

Compounds of formula II in which $R^2$ is $C_{1-6}$alkoxy can be made by reacting a compound of formula II in which $R^2$ is chlorine with sodium$C_{1-6}$alkoxide in the corresponding alcohol at about reflux for about five hours. Compounds of formula II in which $R^2$ is $NR^6R^7$, where $R^6$ and $R^7$ are as defined above, can be made by reacting the compound of formula I in which $R^2$ is chlorine with a compound of formula $HNR^6R^7$ generally in a solvent such as ethanol at about 100° C. for about 24 hours.

Compounds of formula V in which $R^2$ is hydrogen, Y is N and X and Z are $CR^8$ can be made by reacting a compound of formula VIII:

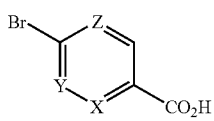

(VIII)

successively with a strong base, such as 2,2,6,6-tetramethylpiperidine mixed with n-butyllithium generally at a temperature of about −78° C. in a solvent such as tetrahydrofuran for about 90 minutes, then with dimethylformamide generally at about room temperature for several hours, then with hydrazine generally also in a solvent such as tetrahydrofuran followed by heating to reflux in the presence of a base such as potassium acetate. Addition of the Ar group to the resulting bromopyrido pyridazinone can occur via a Stille coupling as described above. The resulting compound is converted into the compound of formula V using phosphorus oxychloride as described above.

Compounds of formula I can be converted to other compounds of formula I by standard methods.

Where the synthesis of intermediates and starting materials is not described these compounds are commercially available or can be made from commercially available compounds by standard methods.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples serve to illustrate the preparation of compounds of the present invention.

INTERMEDIATES

Intermediate I

Preparation of 6-bromo-1-chlorophthalazine

Described in WO-A-0281474.

Intermediate II

6-Bromo-N-(4-trifluoromethylphenyl)-1-phthalazinamine

To Intermediate I (2 g; 8.21 mmol) and 4-aminobenzotrifluoride (1.32 g 1.024 mL; 8.21 mmol) in 1,4-dioxane (20 mL) was added 1 drop of conc. HCl. The reaction mixture was heated at reflux for 1 h. After cooling to room temperature the insoluble material was collected by filtration, washed with 1,4-dioxane and dried. The solid was dissolved in ethyl acetate and washed with saturated sodium carbonate. The ethyl acetate extracts were combined, washed with brine, dried over magnesium sulphate, filtered and evaporated under reduced pressure to give a solid. The solid was rinsed with ethanol, the insoluble material was collected by filtration and dried at 60° C. under vacuum to give 1.1 g of product. $^1$H NMR (400 MHz) DMSO-d$^6$ δ: 7.72 (2H, d, J 8.6), 8.18-8.23 (3H, m), 8.39 (1H, d, J 2.0), 8.58 (1H, d, J 9.0), 9.20 (1H, s), 9.61 (1H, s).

Similarly prepared were:

Intermediate III

6-Bromo-N-(4-trifluoromethoxyphenyl)-1-phthalazinamine $^1$H NMR (400 MHz) DMSO-d$^6$ δ: 7.38 (2 H, d, J 8.2), 8.02 (2 H, dd, J 2.0 and 8.2), 8.21 (1 H, dd, J 1.8 and 8.8), 8.36 (1 H, d, J 1.6), 8.55 (1 H, d, J 9.0), 9.13 (1 H, s), 9.39-9.60 (1 H, m); MS (ES M+1) 384/386.

Intermediate IV

6-Bromo-N-(4-tert-butylphenyl)-1-phthalazinamine $^1$H NMR (400 MHz) DMSO-d$^6$ δ: 1.31 (9 H, s), 7.38 (2 H, d, J 8.6), 7.79 (2 H, d, J 7.8), 8.16 (1 H, dd, J 1.6 and 9.0), 8.31 (1 H, d, J 1.6), 8.54 (1 H, d, J 9.0), 9.07 (1 H, s), 9.20 (1 H, s); MS (ES M+1) 356/358.

Intermediate V

6-Bromo-N-(4-ethoxycarbonylphenyl)-1-phthalazinamine $^1$H NMR (400 MHz) DMSO-d$^6$ δ: 1.33 (3H, t, J 7.0 Hz), 4.32 (2H, q, J 7.0 Hz), 7.97 (2H, d, J 9.0 Hz), 8.12 (2H, d, J 9.0 Hz), 8.23 (1H, dd, J 2.0 and 9.0 Hz), 8.39 (1H, d, J 2.0 Hz), 8.59 (1H, d, J 9.0 Hz), 9.21 (1H, s), 9.62 (1H, s).

Intermediate VI

6-Bromo-1,4-dichlorophthalazine

5-Bromo-1,3-isobenzofurandione (14.8 g, 65.4 mmol) was suspended in acetic acid (150 mL), and treated with hydrazine hydrate at (10 mL) at 80° C. overnight. The mixture was cooled, filtered, and the residue was washed with methanol. The residue was triturated with 4M NaOH (ca. 250 mL), and filtered. The pale yellow filtrate was acidified with conc. HCl and filtered. The residue was azeotroped with toluene (×4), and suspended in POCl$_3$ (75 mL). N,N-diisopropylethylamine (10 mL) was slowly added and the mixture was heated to reflux for 3 h and then concentrated under reduced pressure, suspended in chloroform and filtered. The filtrate was poured onto ice, and the organic phase was washed with sodium bicarbonate solution, followed by brine. The organic phase was dried (sodium sulfate) and filtered through a pad of silica, eluting with chloroform, which after evaporation gave an off-white solid (6.5 g, 36%). $^1$H NMR (400 MHz) CDCl$_3$ δ: 8.14-8.20 (2H, m), 8.48 (1H, d, J 0.4); MS (ES M+1) 279.

Intermediate VII

6-Bromo-4-chloro-N-(4-trifluoromethylphenyl)-1-phthalazinamine hydrochloride Intermediate VI (3.29 g, 11.8 mmol) and 4-aminobenzotrifluoride (1.91 g, 11.84 mmol) were suspended in ethanol and heated to reflux for 3 h. The mixture was filtered to give a pale-yellow solid (3.0 g); MS (ES M+1) 404.

Intermediate VIII

6-Bromo-4-methoxy-N-(4-trifluoromethylphenyl)-1-phthalazinamine

Intermediate VII (1.8 g, 3.96 mmol) and sodium methoxide (2.14 g, 39.6 mmol) were suspended in dry methanol (15 mL), and heated to reflux for 5 h. The mixture concentrated under reduced pressure and the residue was partitioned between EtOAc/ammonium chloride, and the aqueous phase was extracted with EtOAc (×2). The combined organic phases were washed (brine), dried (sodium sulfate) and concentrated to give a pale yellow solid, which was recrystallized from DCM to give a white solid (175 mg, 46%). $^1$H NMR (400 MHz) DMSO-d$^6$ δ: 4.14 (3H, s), 7.67 (2H, d, J 8.8), 8.10 (2H, d, J 8.8), 8.22-8.28 (2H, m), 8.51 (1H, d, J 8.4), 9.38 (1H, s); MS (ES M+1) 398/400.

Intermediate IX

6-Bromo-4-dimethylamino-N-(4-trifluoromethylphenyl)-1-phthalazinamine

Intermediate VII (107 mg, 0.24 mmol) was treated with dimethylamine (30% in ethanol, 3 mL) in a sealed tube at 100° C. for 24 h. The mixture was concentrated under reduced pressure, and the resulting residue was partitioned between DCM/sodium bicarbonate solution. The aqueous phase was extracted with DCM, and the combined organic phases were dried (sodium sulfate) and concentrated to give a yellow oil (87 mg) and used in the coupling step without further purification. MS (ES M+1) 411/413.

Intermediate X

6-Bromo-4-(morpholin-4-yl)-N-(4-trifluoromethylphenyl)-1-phthalazinamine

Intermediate VII (100 mg, 0.23 mmol) was suspended in ethanol (2 mL) and treated with morpholine (0.099 mL, 1.14 mmol) in a sealed tube at 100° C. for 24 h. The resulting mixture was concentrated under reduced pressure, and the resulting residue was partitioned between DCM/sodium bicarbonate solution. The aqueous phase was extracted with DCM, and the combined organic phases were dried (sodium sulfate) and concentrated to give a yellow oil, which was used without further purification. MS (ES M+1) 453/455.

Intermediate XI

7-Bromo-3H-pyrido[3,4-d]pyridazin-4-one 2,2,6,6-Tetramethylpiperidine (9.58 mL, 56.4 mmol) was dissolved in dry THF (100 mL), and cooled to 0° C., whilst n-butyllithium (1.6M in hexanes, 35.2 mL, 56.43 mmol) was added over 15 min. The resulting solution was cooled to −78° C., and 6-bromonicotinic acid (3.8 g, 18.8 mmol.) was added as a solid in four equal portions, with stirring over 10 min. Stirring was continued at this temperature for 1.5 h, and the resulting deep-red solution was treated with dry DMF (10 mL) and allowed to warm to room temperature overnight. The mixture was poured onto water (200 mL) and acidified with 1M HCl, and the aqueous phase was extracted with EtOAc (×4). The combined organic phases were washed (brine), dried (sodium sulfate) and concentrated to give a yellow oil, which was dissolved in THF (25 mL) and treated with hydrazine (1M in THF, 19 mL). The precipitate was filtered, and dissolved in ethanol (50 mL) and heated to reflux in the presence of potassium acetate (5 g). The mixture was concentrated under reduced pressure and the brown oily solid was triturated with diethyl ether and the ethereal solution was subjected to flash chromatography (50% ethyl acetate/isohexane) to give a white solid (0.5 g, 12%). $^1$H NMR (400 MHz) DMSO-d$^6$ δ: 8.21 (1H, s), 8.36 (1H, s), 9.20 (1H, s), 13.09, (1H, s). MS (ES M+1) 226/228.

Intermediate XII

7-(3-Methylpyridin-2-yl)-3H-pyrido[3,4-d]pyridazin-4-one

Intermediate XI (104 mg, 0.46 mmol), anhydrous lithium chloride (59 mg, 1.38 mmol), 3-methyl-2-tributylstannylpyridine (264 mg, 0.69 mmol), CuI (8.8 mg, 0.05 mmol) and Pd(PPh$_3$)$_4$ (26.6, 0.02 mmol) were suspended in dioxane (4 mL) and irradiated with microwave radiation at 160° C. for 15 min. The mixture was filtered, washing the residue with EtOAc. The residue was triturated with hot methanol filtered and the filtrate was concentrated to give a white solid (83 mg, 76%). $^1$H NMR (360 MHz) DMSO-d$^6$ δ: 2.56 (3H, s), 6.68 (1H, br), 7.06 (1H, d, J 6.3 Hz), 7.31 (1H, br), 7.62-7.90 (2H, br m), 8.82 (1H, br). MS (ES M+1) 239.

Intermediate XIII

6-(4,4,5,5-Tetramethyl[1,3,2]dioxaborolan-2-yl)-N-(4-trifluoromethylphenyl)-1-phthalazinamine Intermediate II (1.5 g; 4.07 mmol), bis(pinacolato)diboron (1.14 g; 4.48 mmol), potassium acetate (0.80 g; 8.15 mmol) and [1,1'-bis(diphenylphosphino)ferrocene]palladium(II) chloride (0.15 g; 0.20 mmol) in 1,4-dioxane (50 mL) were heated at 100° C. for 18 h. The solvent was evaporated under reduced pressure and the residue partitioned between ethyl acetate and water. The ethyl acetate extracts were combined, washed with brine, dried over magnesium sulphate, filtered through Hyflo and evaporated under reduced pressure to give a solid. The solid was tritiated with hexane and collected by filtration and dried to give 1.8 g of the title compound. $^1$H NMR (360 MHz) DMSO-d$^6$ δ: 1.37 (12 H, s), 7.71 (2H, d, J 8.6), 8.22 (3H, m), 8.43 (1H, s), 8.62 (1H, d, J 8.2 Hz), 9.33 (1H, s), 9.59 (1H, s). MS (ES M+1) 416.

Intermediate XIV

2-Chloro-3-(1-fluoro-1-methylethyl)pyridine

To a solution of 2-(2-chloro-3-pyridinyl)propan-2-ol (1 g; 5.83 mmol) in dichloromethane (10 mL) cooled to −70° C. was added diethylaminosulphur trifluoride (1.1272 g; 0.857 mL; 6.993 mmol) dropwise. On completion of the addition the reaction mixture was allowed to warm to room temperature and stir for 30 min. TLC showed starting material consumed. The reaction mixture was poured onto sodium carbonate solution and extracted with dichloromethane. The dichloromethane extracts were combined, washed with water, dried over magnesium sulphate filtered and evaporated under reduced pressure to give an oil. Yield=0.9 g. $^1$H NMR (360 MHz) DMSO-d$^6$ δ: 1.83 (3H, s), 1.89 (3H, s), 7.30 (1H, dd, J 4.6 and 7.7 Hz), 8.00 (1H, dd, J 1.9 and 7.9 Hz), 8.34 (1 H, dd, J 1.9 and 4.7 Hz).

Intermediate XV 2-(3-Trifluoromethyl-2-pyridinyl)pyrido[2,3-d]pyridazin-5-one

A 3M solution of methylmagnesium iodide in ether (100 mL, 0.3 mol) was added to dry THF (300 mL) cooled in an ice bath. A solution of 3-trifluoromethyl-2-pyridinecarbonitrile (41 g, 0.24 mol) in dry THF (100 mL) was then added under N$_2$, such that the internal temperature did not exceed 10° C. When addition was complete (20 min) the mixture was stirred at room temperature for 1 h. The mixture was then quenched with a saturated aqueous solution of ammonium chloride (100 mL) followed by 2N HCl (200 mL). The product, 1-(3-trifluoromethyl-2-pyridinyl)ethanone, was extracted into ether (3×200 mL) and isolated as a brown oil (34 g). TLC: silica, EtAc:Hexane 1:3; Rf, 0.6. $^1$H NMR (360 MHz) CDCl$_3$ δ: 2.62 (3H, s), 7.45-7.49 (1H, m), 8.01 (1H, dd, J 0.8 and 8.1 Hz), 8.71 (1H, dd, J 0.8 and 8.1 Hz).

A mixture of the ethanone (2.8 g, 0.015 mol) and dimethylformamide dimethyl acetal (2.0 mL, 0.015 mol) was heated in a microwave apparatus at 160° C. for 10 min. This was repeated (×12) and the resulting dark oil was added to ethyl 3-aminocrotonate (40 g, 0.31 mol) in glacial acetic acid (500 mL) and heated conventionally at reflux for 18 h. The mixture was then concentrated and partitioned between diethyl ether (3×300 mL) and 2N NaOH solution (200 mL). The organic phase was washed with brine (200 mL), dried MgSO$_4$) and concentrated to give a brown oil that was purified by column chromatography on silica with EtAc:Hexane 1:3->1:1 as eluant to give ethyl 2-methyl-6-(3-trifluoromethyl-2-pyridinyl)pyridine-3-carboxylate as an oil (36 g). TLC:silica, EtAc:Hexane 1:1; Rf, 0.5. $^1$H NMR (360 MHz) CDCl$_3$ δ: 1.43 (3H, t, J 7.2 Hz), 2.90 (3H, s), 4.42 (2H, q, J 7.2 Hz), 7.48-7.51 (1H, m), 7.60 (1H, d, J 8.0), 8.13 (1H, dd, J 0.8 and 8.1 Hz), 8.33 (1H, d, J 8.0 Hz), 8.85 (1H, d, J 8.1 Hz).

The ethyl carboxylate (36 g, 0.12 mol), N-bromosuccinimide (72 g, 0.4 mol) and dibenzoyl peroxide (1 g) in carbon tetrachloride (700 mL) were heated at reflux for 72 h and illuminated with a desk lamp. The mixture was then filtered, and the mother liquor washed with 2M KOH solution (100 mL). The organic phase was dried (MgSO$_4$)and concentrated to give a 1:9 mixture of mono- and dibromomethyl derivatives (50 g). This was dissolved in ethanol (250 mL), hydrazine hydrate (25 mL) added and the mixture heated at reflux for 18 h. The mixture was concentrated, the residue triturated with water and Intermediate XV was collected by filtration as a yellow solid (16 g). TLC: silica, EtAc; Rf, 0.5. $^1$H NMR (400 MHz) DMSO-d$^6$ δ: 7.80-7.85 (1H, m), 8.20 (1H, d, J 8.3 Hz), 8.41 (1H, s), 8.44 (1 H, dd, J 1.1 and 8.0 Hz), 8.74 (1H, d, J 8.3 Hz), 8.01 (1H, d, J 8.0 Hz).

Intermediate XVI 2-(3-Trifluoromethyl-2-pyridinyl)pyrido[2,3-d]pyridazin-5-amine Intermediate XV (0.4 g, 0.0014 mol) was heated in POCl$_3$ at reflux for 1 h. The excess POCl$_3$ was then removed in vacuo and chased with toluene (×2). 150 mg of the residue was taken up in 33% aqueous ammonia (3 ml) and heated in a Smith microwave reactor for 30 min at 140° C. to give Intermediate XVI $^1$H NMR (400 MHz), DMSO-d$^6$ δ: 8.83 (1H, dd, J 4.8, 0.8 Hz), 8.77 (1H, d, J 0.4 Hz), 8.69 (1H, dd, J 8.4, 0.8 Hz), 8.27 (1H, dd, J 8.4, 1.6 Hz), 8.05 (1H, d, J, 8.4 Hz), 7.66-7.63 (1H, m), 7.21 (2H, s).

EXAMPLES

Example 1

N-(4-Trifluoromethylphenyl)-6-(3-trifluoromethyl-2-pyridinyl)-1-phthalazinamine

To Intermediate II (300 mg; 0.815 mmol), bis(pinacolato)diboron (227 mg; 0.90 mmol), potassium acetate (159.96 mg; 1.63 mmol) and [1,1'bis(diphenylphosphino)ferrocene] palladium(II)chloride (29.81 mg; 0.041 mmol) stirred under nitrogen for ten minutes was added 1,4-dioxane (10 mL). The reaction mixture was heated at reflux for 18 h. After allowing to cool, 2-chloro-3-trifluoromethylpyridine (148 mg; 0.8149 mmol), 2M sodium carbonate solution (1 mL) and [1,1'bis(diphenylphosphino)ferrocene]palladium(II) chloride (29.81 mg; 0.041 mmol) was added and the reaction mixture was heated at 100° C. for 6 h. MS indicated product formation. The reaction mixture was filtered through celite and washed with ethyl acetate. The organic solution was washed with brine, dried over magnesium sulphate, filtered and evaporated under reduced pressure to give an oil. The oil was purified on a silica column using a hexane/ethyl acetate gradient. The appropriate fractions were combined and evaporated under reduced pressure to give a solid. The solid was tritiated with hexane and collected by filtration to give the title compound Yield=135 mg (38%). $^1$H NMR (400 MHz) DMSO-d$^6$ δ: 7.73 (1H, s), 7.75 (1H, s), 7.80 (1H, dd, J 4.9 and 7.6), 8.13 (1H, d, J 8.6), 8.19-8.24 (3H, m), 8.44 (1H, dd, J 1.2 and 8.2), 8.74 (1H, d, J 8.6), 9.01 (1H, d, J 4.3), 9.33 (1H, s), 9.66 (1H, s); MS (ES M+1) 435.

Similarly prepared were:

Example 2

6-(3-Fluoro-2-pyridinyl)-N-(4-trifluoromethylphenyl)-1-phthalazinamine $^1$H NMR (400 MHz) DMSO-d$^6$ δ: 7.61-7.65 (1H, m), 7.73 (2H, d, J 8.6), 7.96 (1 H, d, J 1.2), 7.99 (2 H, dd, J 1.4 and 3.3), 8.01 (1 H, d, J 1.2), 8.23 (2 H, d, J 8.6) 8.56-8.58 (1H, m), 8.63 (1H, s), 8.67-8.69 (1 H, m), 8.75 (1H, s), 8.77 (1 H, s), 9.38 (1 H, s), 9.64 (1 H, s); MS (ES M+1) 385.

Example 3

N-(4-(tert-Butylphenyl)-6-(3-trifluoromethyl-2-pyridinyl)-1-phthalazinamine $^1$H NMR (360 MHz) DMSO-d$^6$ δ: 1.32 (9H, s), 7.40 (2H, d, J 8.8), 7.79 (1H, dd, J 4.7 and 7.9), 7.84 (2H, d, J 8.4), 8.05-8.12 (2H, m), 8.42 (1H, dd, J 0.7 and 7.4), 8.69 (1H, d, J 8.8), 9.00 (1H, d, J 4.6), 9.18 (1H, s), 9.22 (1H, s); MS (ES M+1) 423.

Example 4

6-(3-Methyl-2-pyridinyl)-N-(4-(trifluoromethyl)phenyl)-1-phthalazinamine

To Intermediate II (300 mg; 0.815 mmol), 3-methyl-2-(tributylstannyl)pyridine (467 mg; 1.22 mmol), lithium chloride anhydrous (77 mg; 1.83 mmol) and copper(I)iodide (5.8 mg; 0.03 mmol) in dioxane (3 mL) was added tetrakis(triphenylphosphine)palladium(0) (35 mg; 0.03 mmol). The reaction mixture was heated at 150° C. for 15 min in a Smith Microwave reactor. The catalyst was collected by filtration through a celite pad and washed with ethyl acetate. The filtrate washed with brine, the ethyl acetate extracts were combined, dried over magnesium sulphate, filtered and evaporated under reduced pressure to give an oil. The oil was purified by flash chromatography using a gradient elution, hexane/ethyl acetate (10:1) to ethyl acetate. The appropriate fractions were combined and evaporated under reduced pressure to give a solid. The solid was recrystallized from acetonitrile, solid collected by filtration and dried. Yield=150 mg (48%). $^1$H NMR (400 MHz) DMSO-d$^6$ δ: 2.43 (3H, s), 7.43 (1H, dd, J 4.7 and 7.8 Hz), 7.73 (2H, d, J 8.6 Hz), 7.84 (1H, dd, J 1.0 and 7.6 Hz), 8.23-8.28 (4H, m), 8.59 (1H, dd, J 1.0 and 4.5 Hz), 8.72 (1H, d, J 8.6 Hz), 9.31 (1H, s), 9.62 (1H, s); MS (ES M+1) 381.

Similarly prepared were:

Example 5

6-(3-Methyl-2-pyridinyl)-N-(4-trifluoromethoxyphenyl)-1-phthalazinamine $^1$H NMR (400 MHz) DMSO-d$^6$ δ: 2.43 (3H, s), 7.42-7.45 (3H, m), 7.86 (1H, dd, J 0.8 and 7.8 Hz), 8.00 (2H, d, J 9.0 Hz), 8.31-8.36 (2H, m), 8.61 (1H, dd, J 0.8 and 4.7 Hz), 8.80 (1H, d, J 8.6 Hz), 9.31 (1H, s); MS (ES M+1) 397.

Example 6

6-(2-Pyridinyl)-N-(4-trifluoromethylphenyl)-1-phthalazinamine $^1$H NMR (400 MHz) DMSO-d$^6$ δ: 7.58 (1H, dd, J 1.2 and 2.7), 7.88 (2H, d, J 8.6), 8.03 (2H, d, J 8.6), 8.07-8.12 (1H, m), 8.33 (1H, d, J 8.2), 8.84-8.85 (1H, m) 9.04 (1H, dd, J 2.0 and 8.6), 9.17 (2H, dd, J 1.6 and 7.4), 9.70 (1H, s), 11.05-11.26 (1H, br s); MS (ES M+1) 367.

Example 7

N-(4-Trifluoromethylphenyl)-2-(3-trifluoromethyl-2-pyridinyl)pyrido[2,3-d]pyridazin-5-amine Intermediate XV (0.4 g, 0.0014 mol) was heated in POCl$_3$ at reflux for 1 h. The excess POCl$_3$ was then removed in vacuo and chased with toluene (×2). The residue was dissolved in dioxane (10 mL), 4-aminobenzotrifluoride (0.45 g, 0.0028 mol) added and the mixture heated at reflux for 30 min. The mixture was concentrated and purified by chromatography on silica with EtOAc:Hexanes->EtOAc as eluent and the product recrystallised from ethanol to afford the title compound as an off-white solid (50 mg). $^1$H NMR (360 MHz), DMSO-d$^6$ δ: 7.76 (2H, d, J 8.5 Hz), 7.8-7.9 (1H, m), 8.23 (2H, d, J 8.5 Hz), 8.43 (1H, d, J 8.5 Hz), 8.48 (1H, d, J, 8.5 Hz), 9.05 (1H, s), 9.29-9.24 (2H, m), 9.84 (1H, s).

Example 7a

N-(4-Trifluoromethylphenyl)-2-(3-trifluoromethyl-2-pyridinyl)-pyrido[2,3-d]pyridazin-5-amine benzenesulfonate salt Example 7 was dissolved in DMF at room temperature and benzenesulfonic acid (1.2 eq) added. The solution was aged for 1 h, then slowly diluted with isopropyl acetate over 90 min. After aging for 4 h, the slurry was filtered and the cake was washed with isopropyl acetate. The yellow crystalline solid was dried at room temperature in vacuum to constant weight. Yield 94%.

Example 7b

N-(4-Trifluoromethylphenyl)-2-(3-trifluoromethyl-2-pyridinyl)pyrido[2,3-d]pyridazin-5-amine hydrochloride salt Example 7 was dissolved in hot ethanol and a 2M solution of HCl in ether (excess) added. The suspension was aged for 1 h, the slurry was filtered and the cake was washed with ethanol and ether. The solid was dried at room temperature in vacuum to constant weight. Yield 90%. $^1$H NMR (360 MHz) DMSO-d$^6$ δ: 7.84 (2H, d, 8.6 Hz), 7.85-7.80 (1H, m), 8.11 (1H, dd, J 8.4 Hz), 8.5 (2H, m), 9.05 (1H, d, J 3.8 Hz), 9.33 (1H, s), 9.49 (1H, J 8.6 Hz).

Example 8

6-(1-Methyl-1H-imidazol-2-yl)-N-(4-trifluoromethylphenyl)-1-phthalazinamine

To a stirred solution of N-methylimidazole (97 μL, 1.23 mmol) in tetrahydrofuran (2 mL) at −78° C. was added n-butyllithium (1.6 M in hexanes, 0.82 mL, 1.30 mmol) dropwise. The colorless solution was stirred for 30 mins then zinc chloride (500 mg, 3.6 mmol) in tetrahydrofuran (3 mL) was added via cannula. The reaction was allowed to warm to 0° C. over 1 h and then to room temperature over a further hour. Intermediate II (150 mg, 0.408 mmol) and tetrakis(triphenylphoshine)palladium (23 mg, 8.16 μmol) were dissolved in tetrahydrofuran (2 ml) and added to the reaction mixture via cannula. Nitrogen was then bubbled through the mixture and it was then heated to reflux and stirred for 16 h. After cooling the reaction mixture was poured into a solution of ethylenediaminetetraaceticacid disodium salt (11 g) in 100 mL water. The mixture was then basified by addition of solid sodium bicarbonate, extracted three times with ethyl acetate and dried over sodium sulfate. After filtration, the mixture was pre-adsorbed onto silica gel and purified by column chromatography (5% methanol in methylene chloride). $^1$H NMR (400 MHz, DMSO-d$^6$) δ: 9.60 (1H, s) 9.31 (1H, s), 8.69 (1H, d J 9.0 Hz), 8.42-8.40 (2H, m), 8.22 (2H, d, J 8.6 Hz), 7.72 (2H, d, J 8.6 Hz), 7.41 (1H, s), 7.11 (1H, s), 3.94 (3H, s); MS (MH$^+$) 370.

Example 9

4-Methoxy-6-(3-methyl-2-pyridinyl)-N-(4-trifluoromethylphenyl)-1-phthalazinamine Intermediate VII (100 mg, 0.25 mmol), anhydrous lithium chloride (31 mg, 0.75 mmol), 3-methyl-2-tributylstannylpyridine (144 mg, 0.38 mmol), CuI (4.9 mg, 0.03 mmol.) and Pd(PPh$_3$)$_4$ (14.5 mg, 0.01 mmol) were suspended in dioxane (3 mL) and irradiated with microwave radiation at 160° C. for 15 min. The mixture was filtered and concentrated to give a dark brown oil, which was purified by flash chromatography (25->50% ethyl acetate—isohexane) to give an off-white solid (24 mg, 23%). 1H NMR (500 MHz, DMSO-d$^6$) δ: 2.41 (3H, s), 4.13 (3H, s), 7.41 (1H, dd, J 4.5 and 7.5 Hz), 7.67 (2H, d, J 8.4 Hz), 7.82 (1H, d, J 7.6 Hz), 8.13 (2H, d, J 8.7 Hz), 8.26 (1H, dd, J 1.7 and 8.6 Hz), 8.29 (1H, s), 8.58 (1H, d, J 3.9 Hz), 8.64 (1H, 8.6 Hz), 9.40 (1H, s); MS (ES M+1) 411.

Example 10

7-(3-Methyl-2-pyridinyl)-N-(4-trifluoromethylphenyl)pyrido[3,4-d]pyridazin-4-amine Intermediate XII (83 mg, 0.35 mmol) was suspended in POCl$_3$ (5 mL) and heated to 100° C. for 5 h, and concentrated to dryness. The residue was suspended in dioxane (4 ml), and methanol (4 mL) was added to solubilize the mixture, which was then treated with the 4-trifluoromethylphenylamine (0.217 ml, 1.74 mmol.) at 100° C. overnight. The residue was filtered, partitioned between NaHCO$_3$ (sat. aq.)/DCM, and the aqueous phase was extracted (DCM×2). The combined organic phases were dried (sodium sulfate) and concentrated to give a brown oily residue. Purification by flash chromatography (eluent: 20->100% ethyl acetate/isohexane) gave on off-white solid, (10 mg, 7%)
$^1$H NMR (500 MHz, DMSO-d$^6$) δ: 2.57 (3H, s), 7.46 (1H, dd, J 4.5 and 7.5 Hz), 7.77 (2H, d, J 8.5 Hz), 7.84 (1H, d, J 8.5 Hz), 8.25 (2H, d, J 8.5 Hz), 8.46 (1H, s), 8.60 (1H, d, J 4.0 Hz), 9.44 (1H, s), 9.96 (1H, s), 10.07 (1H, s); MS (ES M+1) 382.

Example 11

4-Dimethylamino-6-(3-methylpyridin-2-yl)-N-(4-trifluoromethylphenyl)-1-phthalazinamine Prepared as described in Example 4 from Intermediate IX. Purified by reversed phase HPLC; MS (ES M+1) 424.

Example 12

6-(3-Methylpyridin-2-yl)-4-(morpholin-4-yl)-N-(4-trifluoromethylphenyl)-1-phthalazinamine Prepared as described in Example 4 from Intermediate X. Purified by reversed phase HPLC; MS (ES M+1) 466.

Example 13

6-(3-Methoxy-2-pyridinyl)-N-(4-trifluoromethylphenyl)-1-phthalazinamine

To Intermediate XIII (250 mg; 0.60 mmol) and 2-chloro-3-methoxypyridine (95 mg; 0.66 mmol) and 1,1'-bis(diphenylphosphino)ferrocene palladium(II)chloride (22 mg; 0.030 mmol) in 1,4-dioxane (4 mL) was added sodium carbonate solution (1 mL). The reaction mixture was heated at 150° C. for 15 min in a Smith microwave reactor. The reaction mixture was poured into water and extracted with ethyl acetate. The ethyl acetate extracts were combined, washed with brine, dried over magnesium sulphate, filtered and evaporated under reduced pressure. The residue was purified by flash chromatography using ethyl acetate as eluant. The appropriate fractions were combined and evaporated under reduced pressure to give a solid. The solid was recrystallized from acetonitrile, collected by filtration and dried to give the title compound. Yield=55 mg (23%). $^1$H NMR (500 MHz, DMSO-d$^6$) δ: 3.96 (3H, s), 7.51 (1H, m), 7.71 (1H, d, J 8.8 Hz), 7.73 (2H d J 8.6 Hz) 8.24 (2H, d, J 8.6 Hz) 8.38 (1H, dd J 4.6 and 1.0 Hz), 8.5 (1H, d, 8.4) 8.62 (1H, s), 8.67 (1H, d, J 8.8) 9.33 (1H, s), 9.60 (1H, s); MS (ES M+1) 397.

Similarly prepared were:

Example 14

2-{2-[1-(4-Trifluoromethylphenylamino)phthalazin-6-yl]pyridin-3-yl}propan-2-ol $^1$H NMR (500 MHz, DMSO-d$^6$) δ: 1.33 (6H, s), 2.07 (1H, s), 5.00 (1H, s), 7.48 (1H, dd, J 4.6 and 8.1 Hz), 7.73 (2H, d, J 8.6 Hz), 8.00 (1H, s), 8.01 (1H, s), 8.16 (1H, dd, J 1.3 and 8.2 Hz), 8.24 (2H, d, J 8.6 Hz), 8.52 (1H, dd, J 1.1 and 4.5 Hz), 8.61 (1H, d, J 9.0 Hz), 9.26 (1H, s), 9.58 (1H, s); MS (ES M+1) 425.

Example 15

N-(4-Trifluoromethylphenyl)-6-(5-trifluoromethyl-2-pyridinyl)-1-phthalazinamine $^1$H NMR (400 MHz, DMSO-d$^6$) δ: 7.73 (2H, d, J 8.6 Hz), 8.23 (2H, d, J 8.6 Hz), 8.43-8.50 (2H, m), 8.78 (2H, dd, J 2.3 and 1.6 Hz), 8.90 (1H, s), 9.17 (1H, d, J 1.2 Hz), 9.36 (1H, s), 9.63 (1H, s); MS (ES M+1) 435.

Example 16

N-(4-Trifluoromethylphenyl)-6-(6-trifluoromethyl-2-pyridinyl)-1-phthalazinamine $^1$H NMR (400 MHz, DMSO-d$^6$) δ: 7.74 (2H, d, J 8.6 Hz), 8.02 (1H, d, J 7.4 Hz), 8.23 (2H, d, J 8.6 Hz), 8.33 (1H, t, J 7.8 Hz), 8.58 (1H, d, J 7.8 Hz), 8.73-8.79 (2H, m), 8.84 (1H, d, J 1.2 Hz), 9.39 (1H, s), 9.65 (1H, s); MS (ES M+1) 435.

Example 17

N-(4-Trifluoromethylphenyl)-6-(4-trifluoromethyl-2-pyridinyl)-1-phthalazinamine $^1$H NMR (400 MHz, DMSO-d$^6$) δ: 7.73 (2H, d, J 8.6 Hz), 7.90 (1H, dd, J 0.8 and 5.1 Hz), 8.24 (2H, d, J 8.2 Hz), 8.62 (1H, s), 8.78 (1H, s), 8.84-8.86 (1H, m), 8.96 (1H, d, J 1.6 Hz), 9.07 (1H, d, J 5.1 Hz), 9.35 (1H, s), 9.65 (1H, s); MS (ES M+1) 435.

Example 18

6-(4-Methyl-3-pyridazinyl)-N-(4-trifluoromethylphenyl)-1-phthalazinamine $^1$H NMR (500 MHz, DMSO-d$^6$) δ: 2.43 (3H, s), 7.73-7.77 (3H, m), 8.25 (2H, d, J 8.6 Hz) 8.32 (1H, m), 8.39 (1H, s), 8.78 (1H, d, J 8.8 Hz), 9.18 (1H, d, J 5.1 Hz), 9.34 (1H, s), 9.66 (1H, s).

Example 19

6-(5-Methyl-4-pyrimidinyl)-N-(4-trifluoromethylphenyl)-1-phthalazinamine $^1$H NMR (500 MHz, DMSO-d$^6$) δ: 2.61 (3H, s), 7.73 (2H, d, J 8.6 Hz), 8.23 (2H, d, J 8.3 Hz), 8.28 (1H, s), 8.79 (2H, s), 8.94 (1H, s), 9.23 (1H, s), 9.36 (1H, s) 9.65 (1H, s).

Example 20

6-(3-Methyl-2-pyrazinyl)-N-(4-trifluoromethylphenyl)-1-phthalazinamine $^1$H NMR (500 MHz, DMSO-d$^6$) δ: 2.67 (3H,s), 7.73 (2H, d, J 8.8Hz), 8.23 (2H, d, J 8.6 Hz), 8.32 (1H, m), 8.39 (1H, s), 8.65 (2H, m), 8.75 (1H, d, J 8.6Hz), 9.33 (1H, s), 9.64 (1H, s).

Example 21

N-(4-Trifluoromethylphenyl)-6-(4-trifluoromethyl-3-pyridazinyl)-1-phthalazinamine $^1$H NMR (500 MHz, DMSO-d$^6$) δ: 7.66 (2H, d, J 8.6 Hz), 8.1 (2H, d, J 8.6 Hz), 8.21 (1H, d, J 8.6 Hz), 8.24 (1H, d, J 5.4 Hz), 8.29 (1H, s), 8.66 (1H, d, J 8.6 Hz), 9.22 (1H, s), 9.61 (1H, d, J 5.5 Hz).

Example 22

N-(4-tert-Butylphenyl)-6-(3-methyl-2-pyridinyl)-1-phthalazinamine hydrochloride

1-Chloro-6-(3-methyl-2-pyridinyl)phthalazine (200 mg; 0.78 mmol) and 4-tert-butylaniline (117 mg, 0.125 mL; 0.78 mmol) in 1,4-dioxane were heated at reflux for 2 h. After allowing to cool down to room temperature the precipitate was collected by filtration washed with 1,4-dioxane and dried to give the title compound (135 mg) (43%). $^1$H NMR (500 MHz, DMSO-d$^6$) δ: 1.35 (9H, s), 7.48 (1H, dd, J 4.9 and 7.6 Hz), 7.55-7.61 (4H, m), 7.90 (1H, dd, J 0.8 and 7.8 Hz), 8.47 (1H, dd, J 1.6 and 8.6 Hz), 8.52 (1H, d, J 2.0 Hz), 8.63 (1H, dd, J 1.2 and 4.7 Hz), 9.09 (1H, d, J 8.6), 9.32 (1H, s); MS (ES M+1) 369.

Similarly prepared was:

Example 23

N-(4-Fluorophenyl)-6-(3-methyl-2-pyridinyl)-1-phthalazinamine $^1$H NMR (500 MHz, DMSO-d$^6$) δ: 2.42 (3H, s), 7.22 (2H, t, J 8.8), 7.42 (1H, dd, J 4.7 and 7.4), 7.83 (1H, d, J 7.8), 7.98 (2H, dd, J 5.1 and 8.2), 8.19-8.22 (2H, m), 8.58 (1H, d, J 3.9), 8.66 (1H, d, J 8.6), 9.20 (1H, s), 9.28 (1H, s).

Example 24

6-(2-Methoxyphenyl)-N-(4-trifluoromethylphenyl)-1-phthalazinamine

Intermediate II (200 mg; 0.54 mmol), 2-methoxyphenylboronic acid (123.8 mg; 0.814 mmol) and 1,1'-bis(diphenylphosphino)ferrocene]palladium(II)chloride (0.0199 g; 0.027 mmol) was added sodium carbonate solution (1 mL) and 1,4-dioxane (4 mL). The reaction mixture was heated in a Smith microwave reactor for 15 min at 150° C. to product MS (ES M+1) 396. The reaction mixture was poured into water and extracted with dichloromethane. The dichloromethane extracts were combined, dried over magnesium sulphate, filtered and evaporated under reduced pressure to give an oil. The oil was purified by flash chromatography using gradient elution (90->50%) iso-hexane/ethyl acetate (1:1). The appropriate fractions were combined and evaporated under reduced pressure to give a solid. The solid was recrystallized from acetonitrile, collected by filtration and dried to give the title compound (0.095 g; 44%). $^1$H NMR (400 MHz, DMSO-d$^6$) δ: 3.83 (3H, s), 7.11-7.15 (1H, m), 7.22 (1H, d, J 8.2 Hz), 7.45-7.51 (2H, m), 7.72 (2H, d, J 8.6 Hz), 8.17 (1H, s), 8.23 (2H, d, J 8.2 Hz), 8.63 (1 H, d, J 8.6), 9.26 (1 H, s), 9.56 (1 H, s); MS (ES M+1) 396.

Example 25

6-(2-Cyanophenyl)-N-(4-trifluoromethylphenyl)-1-phthalazinamine

The title compound was prepared from 2-(4,4,5,5-tetramethyl[1,3,2]dioxaborolan-2-yl)benzonitrile and Intermediate II using the procedure described in Example 24. $^1$H NMR (400 MHz, DMSO-d$^6$) δ: 7.69-7.75 (3H, m,), 7.83 (1H, d, J 7.0 Hz), 7.91 (1H, m), 8.08 (1H, dd, J 0.8 and 7.8 Hz), 8.24 (1H, d, J 8.6 Hz), 8.27 (1H, dd, J 1.95 and 8.6 Hz), 8.32 (1H d, J 1.2 Hz) 8.78 (1H, d, J 8.6 Hz), 9.33 (1H, s), 9.66 (1H, s); MS (ES M+1) 391.

Example 26

3-(3-Methylpyridin-2-yl)-N-(4-trifluoromethylphenyl)pyrido[2,3-d]pyridazin-8-amine To a solution of ethyl 5-bromo-3-methylpyridine-2-carboxylate (1.6 g; 6.95 mmol) and benzoyl peroxide (84.23 mg; 0.347 mmol) in carbon tetrachloride (20 mL) was added N-bromosuccinimide (2.47 g; 13.91 mmol). The reaction mixture was heated at reflux for 3 h. Another equivalent of N-bromosuccinimide and benzoyl peroxide (85 mg) was added and refluxing was continued for a further 7 h. Reaction was monitored by MS. After 10 h the product was the major peak. The reaction mixture was allowed to cool, filtered through celite washed with carbon tetrachloride. The filtrate was evaporated under reduced pressure to give an oil, 2.7 g. The oil (2.7 g; 6.9615 mmol) and hydrazine hydrate (2.4 mL) in ethanol was heated at reflux overnight. The solvent was evaporated under reduced pressure, the residue was taken-up in water acidified with 2N HCl the solid obtained was collected by filtration washed with water and dried by azeotroping with toluene. Yield=0.9 g. The crude product and phosphorus oxychloride were heated at 60° C. for 1 h. The excess phosphorus oxychloride was evaporated under reduced pressure to give 3-bromo-8-chloropyrido[2,3-d]pyridazine (0.97 g) as solid. This material was azeotroped with toluene and then treated with 4-aminobenzotrifluoride (0.64 g, 0.495 mL; 3.97 mmol) in 1,4-dioxane (20ml) and heated at 40° C. for 1 h. The solvent was evaporated under reduced pressure and the residue partitioned between ethyl acetate and sodium carbonate solution. The ethyl acetate extracts were combined, washed with brine, dried over magnesium sulphate, filtered and evaporated under reduced pressure to give an oil. The oil was purified by flash chromatography using a gradient of (90->50%) iso-hexane/ethyl acetate. The appropriate fractions were combined and evaporated under reduced pressure to give 3-bromo-N-(4-(trifluoromethyl)phenyl)pyrido[2,3-d]pyridazin-8-amine (100 mg). $^1$H NMR (500 MHz, DMSO-d$^6$) δ: 7.73 (2H, d, J 8.6 Hz), 8.41 (2H, d, J 8.8 Hz), 8.91 (1H, d, J 2.2 Hz), 9.25 (1H, s), 9.33 (1H, d, J 2.2 Hz), 10.05 (1H, s).

The amine was reacted as in Example 4 to give the title compound. $^1$H NMR (500 MHz, DMSO-d$^6$) δ: 2.49 (3H, s), 7.49 (1H, dd, J 4.8 and 7.7 Hz), 7.76 (2H, d, J 8.6 Hz), 7.90 (1H, dd, J 0.5 and 7.1 Hz), 8.47 (2H, d, J 8.6 Hz), 8.66 (1H, dd, J 0.5 and 4.2 Hz), 8.80 (1H, d, J 2.0 Hz), 9.39 (1H, s), 9.48 (1H, d, J 2.0 Hz), 10.10 (1H, s); MS (ES M+1) 382.

Following procedures described above the following compounds were prepared:

Example 27

N-(4-Ethoxycarbonylphenyl)-6-(3-methyl-2-pyridinyl)-1-phthalazinamine $^1$H NMR (500 MHz, DMSO-d$^6$) δ: 1.34 (3H, t, J 7.1 Hz), 2.43 (3H, s), 4.33 (2H, q, J 7.1 Hz), 7.42 (1H, dd, J 4.8 and 7.7 Hz), 7.84 (1H, dd, J 0.7 and 7.6 Hz), 7.98 (2H, d, J 8.8 Hz), 8.17 (2H, d, J 8.8 Hz), 8.24 (1H, dd, J 1.5 and 8.3 Hz), 8.28 (1 H, s), 8.59 (1H, dd, J 1.1 and 4.8 Hz), 8.72 (1H, d, J 8.8 Hz), 9.32 (1H, s), 9.63 (1H, s).

Example 28

6-(3,5-Difluoro-2-pyridinyl)-N-(4-trifluoromethylphenyl)-1-phthalazinamine $^1$H NMR (500 MHz, DMSO-d$^6$) δ: 7.73 (2H, d, J 8.6 Hz), 8.20-8.25 (3H, m), 8.52 (1H, d, J 8.6 Hz), 8.59 (1H, s), 8.76 (2H, dd, J 6.7 and 2.0 Hz), 9.38 (1H, s), 9.64 (1H, s).

Example 29

6-(3-Cyano-2-pyridinyl)-N-(4-trifluoromethylphenyl)-1-phthalazinamine $^1$H NMR (400 MHz, DMSO-d$^6$) δ: 7.73-7.77 (3H, m), 8.24 (2H, d, J 8.2 Hz), 8.50 (1H, dd, J 1.8 and 8.8 Hz), 8.55-8.59 (2H, m), 8.81 (1H, d, J 8.6 Hz), 9.06 (1H, dd, J 1.8 and 4.9 Hz), 9.38 (1H, s), 9.69 (1H, s).

Example 30

6-(3-Ethoxycarbonyl-2-pyridinyl)-N-(4-trifluoromethylphenyl)-1-phthalazinamine $^1$H NMR (500 MHz, DMSO-d$^6$) δ: 0.98 (3H, t, J 7.1 Hz), 4.15 (2H, q, J 7.1 Hz), 7.67 (1H, dd, J 4.9 and 7.8 Hz), 7.73 (2H, d, J 8.8 Hz), 8.16 (1H, dd, J 2.0 and 8.6 Hz), 8.21-8.25 (3H, m), 8.33 (1H, dd, J 1.7 and 7.8 Hz), 8.69 (1H, d, J 8.6 Hz), 8.92 (1H, dd, J 1.6 and 4.8 Hz), 9.33 (1H, s), 9.63 (1 H, s).

Example 31

6-(3-(1-fluoro-1-methylethyl)-2-pyridinyl)-N-(4-trifluoromethylphenyl)-1-phthalazinamine $^1$H NMR (500 MHz, DMSO-d$^6$) δ: 1.58 (3H, s), 1.62 (3H, s), 7.54-7.57 (1H, m), 7.73 (2H, d, J 8.6 Hz), 8.01-8.04 (3H, m), 8.23 (2H, d, J 8.6 Hz), 8.64 (2H, dd, J 1.6 and 4.8 Hz), 9.27 (1 H, s), 9.60 (1 H, s).

Example 32

N-(4-Trifluoromethylphenyl)-2-(3-chloro-2-pyridinyl)pyrido[2,3-d]pyridazin-5-amine $^1$H NMR (400 MHz), CDCl$_3$ δ: 7.08-7.18 (1H, m), 7.38-7.43 (1H, m), 7.68 (2H, d, J 6.3 Hz), 7.92 (2H, d, J 6.6 Hz), 8.06-8.21 (1H, m), 8.70 (1H, d, J 3 Hz), 8.78-8.88 (1H, m), 8.94-9.01 (1H, m).

Example 33

N-(5-Trifluoromethyl-2-pyridinyl)-2-(3-trifluoromethyl-2-pyridinyl)pyrido[2,3-d]pyridazin-5-amine Intermediate XVI (56.9 mg, 1.96×10$^{-4}$ mol) was dissolved in dioxane (4 ml) and 2-bromo-5-trifluoromethylpyridine (44 mg, 196 μmol), caesium carbonate (90 mg), Xantphos (6.3 mg) and tris(dibenzylideneacetone)dipalladium(0) (4.2 mg) were added. The reaction was degassed (by bubbling with N$_2$) and heated to reflux. After stirring for 16 h the reaction was allowed to cool to room temperature and filtered through celite (washing with ethyl acetate). The reaction was then quenched with saturated sodium bicarbonate, extracted three times with ethyl acetate, dried over sodium sulfate, filtered and concentrated. Column chromatography (30% ethyl acetate in hexanes) was followed by trituration from methanol to give the product (63 mg, 73%) $^1$H NMR (400 MHz), DMSO-d$^6$ δ: 7.93-7.91 (1H, m), 8.24 (1H, dd, J 8.4, 2.4 Hz), 8.39 (1H, d, J 8.4 Hz), 8.42 (1H, d, J 8.1 Hz), 8.55 (1H, dd, J 8.0, 1.2 Hz), 8.60 (1H, d, J 8.1 Hz), 8.85 (1H, s), 9.0 (1H, s), 9.10 (1H, dd, J 4.4, 0.8 Hz), 9.23 (1H, d, J 8.8 Hz).

What is claimed is:

1. A compound of formula (I):

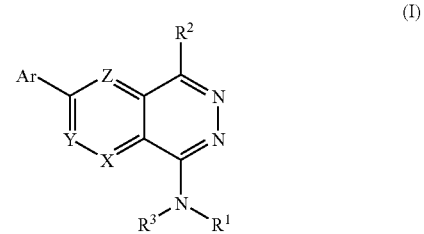

wherein Ar is phenyl, a six-membered heteroaromatic group containing one, two or three nitrogen atoms or a five-membered heteroaromatic group containing one, two, three or four heteroatoms chosen from oxygen, nitrogen and sulfur, at most one heteroatom being oxygen or sulfur, Ar being optionally substituted with one, two or three groups independently chosen from halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, amino, halo$C_{1-6}$alkyl, halo$C_{2-6}$alkenyl, halo$C_{2-6}$alkynyl, hydroxy$C_{1-6}$alkyl, hydroxy$C_{2-6}$alkenyl, hydroxy$C_{2-6}$alkynyl, cyano, nitro, amino$C_{1-6}$alkyl, amino$C_{2-6}$alkenyl, amino$C_{2-6}$alkynyl, $C_{1-6}$alkylsulfonyl, $C_{1-6}$alkylsulfinyl, $C_{1-6}$alkylthio, $C_{1-6}$alkoxycarbonyl, halo$C_{1-6}$alkoxy, halo$C_{2-6}$alkenyloxy, halo$C_{2-6}$alkynyloxy, $NR^4R^5$, $CONR^4R^5$ or $CO_2NR^4R^5$ where each $R^4$ and $R^5$ is independently hydrogen or $C_{1-6}$alkyl;

$R^1$ is phenyl, a six-membered heteroaromatic group containing one, two or three nitrogen atoms or a five-membered heteroaromatic group containing one, two, three or four heteroatoms chosen from oxygen, nitrogen and sulfur, at most one heteroatom being oxygen or sulfur, Ar being optionally substituted with one, two or three groups independently chosen from halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, amino, halo$C_{1-6}$alkyl, halo$C_{2-6}$alkenyl, halo$C_{2-6}$alkynyl, hydroxy$C_{1-6}$alkyl, hydroxy$C_{2-6}$alkenyl, hydroxy$C_{2-6}$alkynyl, cyano, nitro, amino$C_{1-6}$alkyl, amino$C_{2-6}$alkenyl, amino$C_{2-6}$alkynyl, $C_{1-6}$alkylsulfonyl, $C_{1-6}$alkylsulfinyl, $C_{1-6}$alkylthio, $C_{1-6}$alkoxycarbonyl, halo$C_{1-6}$alkoxy, halo$C_{2-6}$alkenyloxy, halo$C_{2-6}$alkynyloxy, $NR^4R^5$, $CONR^4R^5$ or $CO_2NR^4R^5$ where $R^4$ and $R^5$ are as defined above;

$R^2$ is hydrogen, halogen, hydroxy, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $NR^6R^7$ where $R^6$ and $R^7$ are, independently, hydrogen, $C_{1-6}$alkyl or $C_{1-6}$hydroxyalkyl, or $R^6$ and $R^7$, together with the nitrogen atom to which they are attached form a 4, 5 or 6-membered stable heterocycle optionally containing an oxygen ring atom;

$R^3$ is hydrogen or $C_{1-6}$alkyl;

one X, Y and Z is N and the other two are $CR^8$ where $R^8$ is hydrogen, halogen or $C_{1-6}$alkyl;

or a pharmaceutically acceptable salt thereof.

2. A compound according to claim 1 in which Z is N and X and Y are CH.

3. A compound according to claim 1 in which $R^1$ is para-substituted phenyl or pyridyl.

4. A compound according to claim 1, in which Ar is pyridyl monosubstituted at the ring position adjacent to the point of attachment of Ar to the rest of the molecule.

5. A compound according to claim 4 in which $R^2$ is hydrogen, dimethylamino or morpholino.

6. A compound according to claim 1 which is:
   N-(4-trifluoromethylphenyl)-2-(3-trifluoromethyl-2-pyridinyl)pyrido[2,3-d]pyridazin-5-amine;
   7-(3-methyl-2-pyridinyl)-N-(4-trifluoromethylphenyl)pyrido[3,4-d]pyridazin-4-amine;
   3-(3-methylpyridin-2-yl)-N-(4-trifluoromethylphenyl)pyrido[2,3-d]pyridazin-8-amine;
   N-(4-trifluoromethylphenyl)-2-(3-chloro-2-pyridinyl)pyrido[2,3-d]pyridazin-5-amine; and
   N-(5-trifluoromethyl-2-pyridinyl)-2-(3-trifluoromethyl-2-pyridinyl)pyrido[2,3-d]pyridazin-5-amine; or a pharmaceutically acceptable salt thereof.

7. A pharmaceutical composition comprising a compound according to any one of claims 1 or a pharmaceutically acceptable salt thereof and a pharmaceutically acceptable excipient.

8. A method for treating pain, which method comprises administering to a mammalian patient in need thereof a therapeutically effective amount of the compound of claim 1 or a pharmaceutically acceptable salt thereof.

* * * * *